United States Patent
McIntyre

(10) Patent No.: US 10,291,199 B2
(45) Date of Patent: May 14, 2019

(54) DIRECT WRITE SENSORS

(71) Applicant: UT-Battelle, LLC, Oak Ridge, TN (US)

(72) Inventor: Timothy J. McIntyre, Farragut, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 254 days.

(21) Appl. No.: 15/246,907

(22) Filed: Aug. 25, 2016

(65) Prior Publication Data

US 2017/0070204 A1 Mar. 9, 2017

Related U.S. Application Data

(60) Provisional application No. 62/214,233, filed on Sep. 4, 2015.

(51) Int. Cl.
*G01N 29/22* (2006.01)
*H03H 9/02* (2006.01)
(Continued)

(52) U.S. Cl.
CPC ....... *H03H 9/02535* (2013.01); *G01N 29/022* (2013.01); *G01N 29/22* (2013.01); *H01L 41/314* (2013.01); *H03H 9/02007* (2013.01); *H03H 9/02275* (2013.01); *G01N 2291/0255* (2013.01); *G01N 2291/0256* (2013.01); *G01N 2291/0423* (2013.01); *G01N 2291/0426* (2013.01)

(58) Field of Classification Search
CPC .................................................. H03H 9/0235
USPC .............................. 310/313 B, 313 R, 313 D
See application file for complete search history.

(56) References Cited

U.S. PATENT DOCUMENTS 5,571,944 A 11/1996 Pfeifer et al.
5,948,981 A 9/1999 Woodruff
(Continued)

FOREIGN PATENT DOCUMENTS

CN 1012012798 10/2010

OTHER PUBLICATIONS

Stan Farnsworth, "Novacentrix PulseForge TM Curing Copper and other Thin-Film Materials at Production Speeds," Oct. 2009, Available online: http://www.aimcal.org/uploads/4/6/6/9/46695933/farnsworth.pdf.
(Continued)

*Primary Examiner* — Thomas M Dougherty
*Assistant Examiner* — Karen B Addison
(74) *Attorney, Agent, or Firm* — Fox Rothschild LLP

(57) ABSTRACT

A method of making an acoustic wave sensor includes the steps of providing a piezoelectric substrate layer and printing on the substrate layer a sensor layer comprising a first interdigitated acoustic wave transducer, a sensing film, and positioned on an opposing side of the sensing film from the first interdigitated acoustic wave transducer at least one selected from the group consisting of a second interdigitated acoustic wave transducer and a Bragg reflector. An insulation layer can be printed. An antenna can be printed in an antenna layer, and the insulation layer can be interposed between the antenna layer and the sensor layer. An electrical connection can be printed between the antenna and the first interdigitated acoustic wave transducer. An acoustic wave sensor is also disclosed.

2 Claims, 17 Drawing Sheets

(51) Int. Cl.
*H01L 41/314* (2013.01)
*G01N 29/02* (2006.01)

(56) References Cited

U.S. PATENT DOCUMENTS

| | | | |
|---|---|---|---|
| 5,948,982 | A | 9/1999 | Woodruff et al. |
| 6,579,660 | B1 | 6/2003 | Figov |
| 6,716,479 | B2 | 4/2004 | Lu et al. |
| 6,745,627 | B1 | 6/2004 | Woodruff et al. |
| 6,771,071 | B1 | 8/2004 | Wright et al. |
| 6,957,565 | B2 | 10/2005 | Matsiev et al. |
| 6,967,362 | B2 | 11/2005 | Nam et al. |
| 7,043,969 | B2 | 5/2006 | Matsiev et al. |
| 7,220,936 | B2 | 5/2007 | Ott et al. |
| 7,254,990 | B2 | 8/2007 | Matsiev et al. |
| 7,334,452 | B2 | 2/2008 | Matsiev et al. |
| 7,411,494 | B2 | 8/2008 | Kates |
| 7,623,037 | B1 | 11/2009 | Malocha |
| 7,633,206 | B2 | 12/2009 | Andle |
| 7,642,898 | B1 | 1/2010 | Malocha et al. |
| 7,726,184 | B2 | 6/2010 | Cook et al. |
| 7,730,772 | B2 | 6/2010 | Cook et al. |
| 7,755,489 | B2 | 7/2010 | Georgescu et al. |
| 7,777,625 | B1 | 8/2010 | Puccio et al. |
| 7,791,249 | B2 | 9/2010 | Hines et al. |
| 7,825,805 | B2 | 11/2010 | Malocha et al. |
| 7,832,263 | B2 | 11/2010 | Rensel et al. |
| 7,915,785 | B2 | 3/2011 | Andle et al. |
| 7,952,482 | B2 | 5/2011 | Malocha et al. |
| 7,961,105 | B2 | 6/2011 | Puccio et al. |
| 8,094,008 | B2 | 1/2012 | Solie et al. |
| 8,169,320 | B2 | 5/2012 | Malocha et al. |
| 8,441,168 | B2 | 5/2013 | Hines et al. |
| 8,466,776 | B2 | 6/2013 | Fink et al. |
| 8,669,871 | B2 | 3/2014 | Malocha et al. |
| 8,907,769 | B2 | 12/2014 | Haines |
| 8,917,159 | B2 | 12/2014 | McAllister et al. |
| 2003/0035558 | A1 | 2/2003 | Kawamura et al. |
| 2003/0161411 | A1 | 8/2003 | McCorkle et al. |
| 2005/0160821 | A1* | 7/2005 | Cunningham ....... G01N 29/022 73/652 |
| 2005/0281318 | A1 | 12/2005 | Neugebauer |
| 2006/0000285 | A1* | 1/2006 | Edmonson ........... G01N 29/022 73/649 |
| 2006/0121182 | A1 | 6/2006 | Kalyanasundaram et al. |
| 2006/0292777 | A1 | 12/2006 | Dunbar |
| 2007/0007851 | A1 | 1/2007 | Loebl et al. |
| 2009/0315777 | A1 | 12/2009 | Baughman |
| 2010/0245114 | A1 | 9/2010 | Celik-Butler et al. |
| 2010/0272158 | A1 | 10/2010 | Lakkis |
| 2011/0077490 | A1 | 3/2011 | Simpson et al. |
| 2011/0087080 | A1 | 4/2011 | Schroter |
| 2011/0263036 | A1 | 10/2011 | Blauw et al. |
| 2012/0050114 | A1 | 3/2012 | Li et al. |
| 2012/0282594 | A1 | 11/2012 | Chen et al. |
| 2013/0023795 | A1 | 1/2013 | Stein et al. |
| 2013/0040573 | A1 | 2/2013 | Hillyard |
| 2013/0093597 | A1 | 4/2013 | Stolpman |
| 2013/0337190 | A1* | 12/2013 | Ramanujan ............. B41J 3/407 427/559 |
| 2014/0056333 | A1 | 2/2014 | Neff |
| 2014/0111953 | A1 | 4/2014 | McClure et al. |
| 2014/0220724 | A1 | 8/2014 | Duty et al. |
| 2015/0003499 | A1 | 1/2015 | Boutillon et al. |
| 2015/0016487 | A1 | 1/2015 | Britton et al. |
| 2015/0156819 | A1 | 6/2015 | Kielar |

OTHER PUBLICATIONS

"Novacentrix Printed Electronics Product Leadership," Available online: <https://www.novacentrix.com/products/overview>, Jun. 19, 2012, <https://web.archive.org/web/*/https://www.novacentrix.com/products/overview>.

"Novacentrix Inkjet Starter Kits" online: <https://www.novacentrix.com/products/inkjet-starter-kits>.

"Pulse thermal processing—Excellence in Technology Transfer 2013," FLC Southeast Region, Available online: https://www.federallabs.org/index.php?tray=award_detail&cid=FLCawrd743&tid=1FLtop123>.

Tsai et al., "Kasami code-shift-keying modulation for ultra-wideband communication systems", IEEE Trans on Communications (Jun. 2007) 55(6): 1242-1252.

Ver-Bruggen et al., "Humidity sensors designed for buildings seek commercial opportunities", Web. (Aug. 1, 2012).

Virtanen et al., "Inkjet-printed humidity sensor for passive UHF RFID systems", IEEE Trans. on Instrumentation and Measurement (Aug. 2011) 60(8): 2768-2777.

Wang et al., "An all-printed wireless humidity sensor label", Dept of Science and Technology (ITN), Linkping University, SE-601 74, Sweden.

Gold code—Wikipedia, the free encyclopedia [retrieved Aug. 27, 2016], Retrived from Internet: <URL: http://en.wikipedia.org/wiki/Gold code>.

Inverted-F antenna—Wikipedia, the free encyclopedia [retrieved Aug. 27, 2016], Retrived from Internet: <URL: http://en.wikipedia.org/wiki/Inverted-F antenna>.

Feedback shift register—Wikipedia, the free encyclopedia [retrieved Aug. 27, 2016], Retrived from Internet: <URL: http://en.wikipedia.org/wiki/feedback shift register>.

International Search Report mailed in PCT/US16/48577 dated Nov. 18, 2016.

\* cited by examiner

DIRECT WRITE SENSORS

CROSS-REFERENCE TO RELATED APPLICATION

This Application claims priority to U.S. Patent Application No. 62/214,233, filed Sep. 4, 2015, entitled "Direct Write Sensors", the entirety of which is incorporated herein by reference.

STATEMENT REGARDING FEDERALLY SPONSORED RESEARCH

This invention was made with government support under contract No. DE-AC05-00OR22725 awarded by the US Department of Energy. The government has certain rights in this invention.

FIELD OF THE INVENTION

This invention relates generally to acoustic wave sensors, and more particularly to methods and designs for making acoustic wave sensors.

BACKGROUND OF THE INVENTION

Bulk acoustic wave (BAW) and surface acoustic wave (SAW) devices have been fabricated for decades using traditional semiconductor integrated circuit methods. These methods are mature and optimized to produce >1 billion high fidelity, matched filters for RF and microwave communications such as cell phones, walkie-talkies, and other devices. However, relatively sophisticated and expensive equipment is required to produce these devices.

High performance acoustic wave structures have recently been exploited for sensor applications. Acoustic wave structures have been demonstrated to perform as temperature, strain and hydrogen sensing devices, employing traditional photo-lithography for device fabrication. Photo-lithography is time consuming and comparatively expensive, and accordingly new methodologies for manufacturing such sensors are necessary.

SUMMARY OF THE INVENTION

A method of making an acoustic wave sensor includes the steps of providing a piezoelectric substrate layer and printing on the substrate layer a sensor layer comprising a first interdigitated acoustic wave transducer, and at least one other feature selected from the group consisting of a sensing film, an interdigitated acoustic wave transducer, and a Bragg reflector. A second interdigitated acoustic wave transducer or one or more Bragg reflectors can be positioned on an opposing side of the sensing film, if present, from the first interdigitated acoustic wave transducer. An insulation layer can be printed. An antenna can be printed in an antenna layer, and the insulation layer can be interposed between the antenna layer and the sensor layer. An electrical connection can be printed between the antenna and the first interdigitated acoustic wave transducer. The printing method can be performed by aerosol jet direct digital printing.

The acoustic wave sensor can be a bulk acoustic wave sensor. The Q factor of the bulk acoustic wave sensor can be greater than 1000.

The piezoelectric substrate can be provided as a film and moved roll to roll during the printing process.

The method can further include the step of controlling the movement of the aerosol jet thorough a control system and at least one processor.

A plurality of acoustic wave sensors can be printed on the piezoelectric substrate, and the method can further include the step of separating the substrate and the acoustic wave sensors into individual acoustic wave sensors.

The sensing film can include a hydrophilic material. The sensing film can include palladium. The sensing film can include graphene. The sensing film can include a carbon nanotube array. The sensor can have a maximum dimension of less than 2 $mm^2$.

The sensor layer and antenna layer can be printed on opposing sides of the piezoelectric substrate layer. At least a portion of the sensor layer and the antenna layer can be printed simultaneously.

An acoustic wave sensor can include a piezoelectric substrate layer and a sensor layer joined to the substrate layer and comprising a first interdigitated acoustic wave transducer, and at least one other feature selected from the group consisting of a sensing film, an interdigitated acoustic wave transducer, and a Bragg reflector. A second interdigitated acoustic wave transducer or one or more Bragg reflectors can be positioned on an opposing side of the sensing film, if present, from the first interdigitated acoustic wave transducer. All of the interdigitated acoustic wave transducers and Bragg reflector can be aerosol jet printed.

An antenna layer can be provided and an insulation layer can be interposed between the antenna layer and the sensor layer, and the insulation layer and antenna layer can be aerosol jet printed. At least one of the sensor layer and antenna layer can include a dielectric matrix material. The sensor layer and the antenna layer can be printed on opposing sides of the piezoelectric substrate layer.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
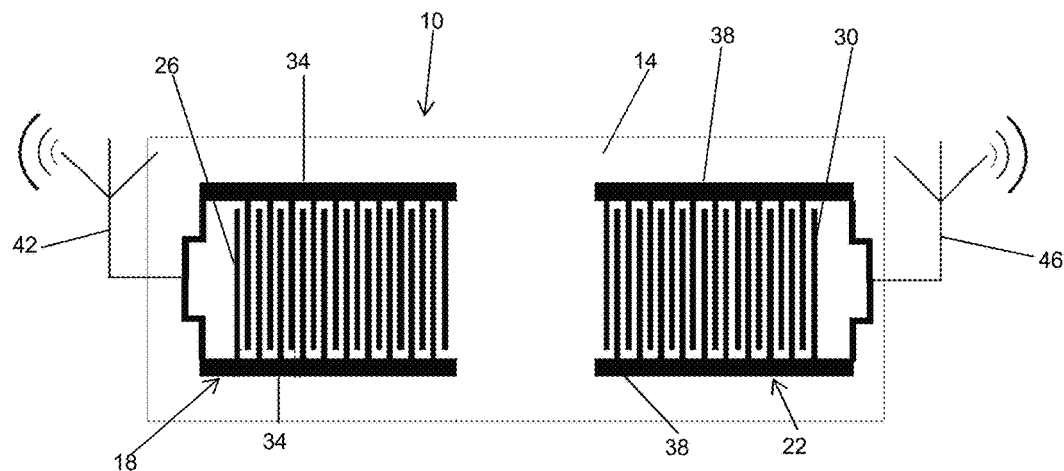
FIG. 1 is a schematic diagram of a surface acoustic wave device according to the invention.

A method of making an acoustic wave sensor includes the steps of providing a piezoelectric substrate layer and printing on the substrate layer a sensor layer comprising a first interdigitated acoustic wave transducer, and at least one other feature selected from the group consisting of a sensing film, an interdigitated acoustic wave transducer, and a Bragg reflector. A second interdigitated acoustic wave transducer or one or more Bragg reflectors can be positioned on an opposing side of the sensing film, if present, from the first interdigitated acoustic wave transducer. An insulation layer can be printed. An antenna can be printed in an antenna layer, and the insulation layer can be interposed between the antenna layer and the sensor layer. The antenna can alternatively be provided separately, and printed or produced by other means. An electrical connection can be printed between the antenna and the first interdigitated acoustic wave transducer. The printing method can be performed by aerosol jet direct digital printing.

The movement of the aerosol jet thorough a control system and at least one processor. Any suitable control mechanism and processor or controller is possible.

A plurality of acoustic wave sensors can be printed on the piezoelectric substrate, and the method can further include the step of separating the substrate and the acoustic wave sensors into individual acoustic wave sensors. The individual sensors can be cut by any suitable device and packaged as individual sensors or groups of sensors.

The sensing film can be any suitable material. The sensing film can for example include a hydrophilic material. The sensing film can include palladium. The sensing film can include graphene. The sensing film can include a carbon nanotube array. The sensor can have a maximum dimension of less than 2 mm². The acoustic wave sensor can be printed without a sensor film to measure temperature, because the piezoelectric material alone can be temperature sensitive in the desired temperature range.

The sensor layer and antenna layer can be printed on opposing sides of the piezoelectric substrate layer. The antenna can connect to more than one sensor. Sensors can be printed on both sides of the piezoelectric substrate layer. Vias can be created through the substrate and suitable electrical connections can be provided through the vias by any suitable method, including aerosol jet printing. At least a portion of the sensor layer and the antenna layer can be printed simultaneously.

An acoustic wave sensor can include a piezoelectric substrate layer and a sensor layer joined to the substrate layer and comprising a first interdigitated acoustic wave transducer, and at least one other feature selected from the group consisting of a sensing film, an interdigitated acoustic wave transducer, and a Bragg reflector. A second interdigitated acoustic wave transducer or one or more Bragg reflectors can be positioned on an opposing side of the sensing film, if present, from the first interdigitated acoustic wave transducer. All of the interdigitated acoustic wave transducers and Bragg reflectors can be aerosol jet printed.

An antenna layer can be provided and an insulation layer can be interposed between the antenna layer and the sensor layer, and the insulation layer and antenna layer can be aerosol jet printed. At least one of the sensor layer and antenna layer can include a dielectric matrix material. The sensor layer and the antenna layer can be printed on opposing sides of the piezoelectric substrate layer. Many antenna designs can be utilized including, without limitation, dipole antennas, gap loaded Archimedean spiral antennas, fractal antennas, and patch antenna arrays.

FIG. 1 is a schematic diagram of a surface acoustic wave device 10 according to the invention. The device 10 includes a piezoelectric substrate 14. An interdigitated transducer 18 has interdigitated transducer lines 26 and contacts 34 which connect to antenna 42. An interdigitated transducer 22 has interdigitated transducer lines 30 and contacts 38 which connect to antenna 46.

Figure 2:
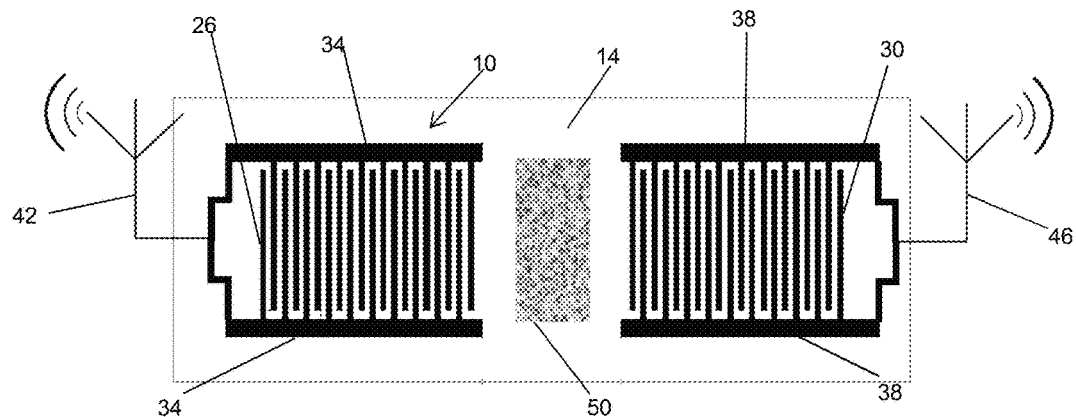
FIG. 2 is a schematic diagram of a surface acoustic wave device functionalized by a chemical specific film.

FIG. 2 is a schematic diagram of the surface acoustic wave device 10 functionalized by a chemical specific film 50. The film 50 can be printed by aerosol jet printing. The film 50 can also be applied by other methods.

Figure 3:
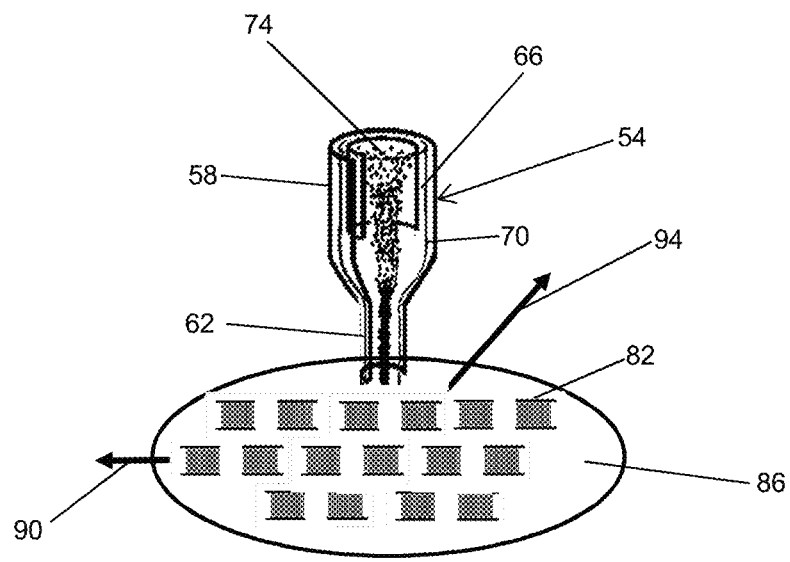
FIG. 3 is a schematic diagram of aerosol jet printing of surface acoustic wave devices on a piezoelectric wafer.

FIG. 3 is a schematic diagram of aerosol jet printing of surface acoustic wave devices on a piezoelectric wafer. An aerosol jet print head 54 includes an outer housing 58 and neck 62. An inner sheath 66 defines an annular space 74 for the flow of sheath gas that serves to focus and direct the aerosol 74 into a fine jet 78. Movement of the print head 54 can be controlled by a processor and control mechanisms to direct the jet 78 so as to create sensors 82 on the substrate 86. The substrate 86 can be in the form of a wafer and can be moved in the direction of arrows 90 and 94 to permit the printing of a multitude of sensors on the same wafer.

Figure 4:
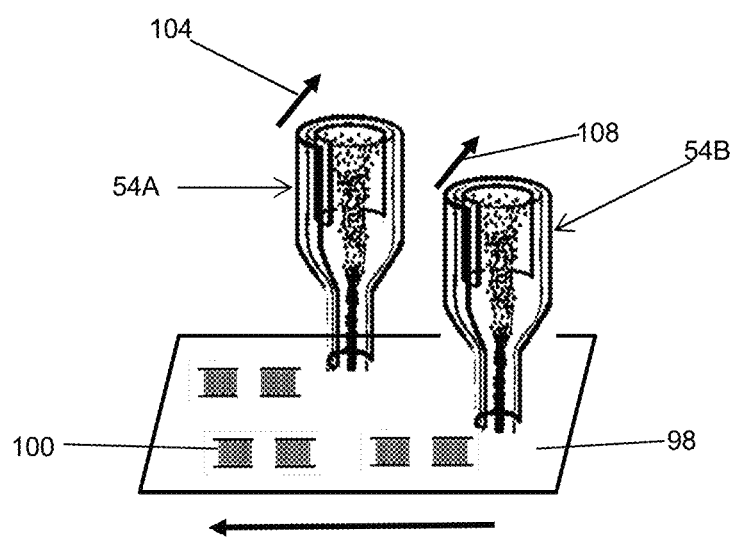
FIG. 4 is a schematic diagram of multi-head printing of surface acoustic wave devices.

FIG. 4 is a schematic diagram of multi-head printing of surface acoustic wave devices. This is shown schematically by print head 54A which moves according to direction arrow 104, and print head 54B which can move in the same or a different direction as shown by arrow 108. Accordingly multiple sensors 100 can be printed rapidly and in some cases simultaneously onto substrate 98.

Figure 5:
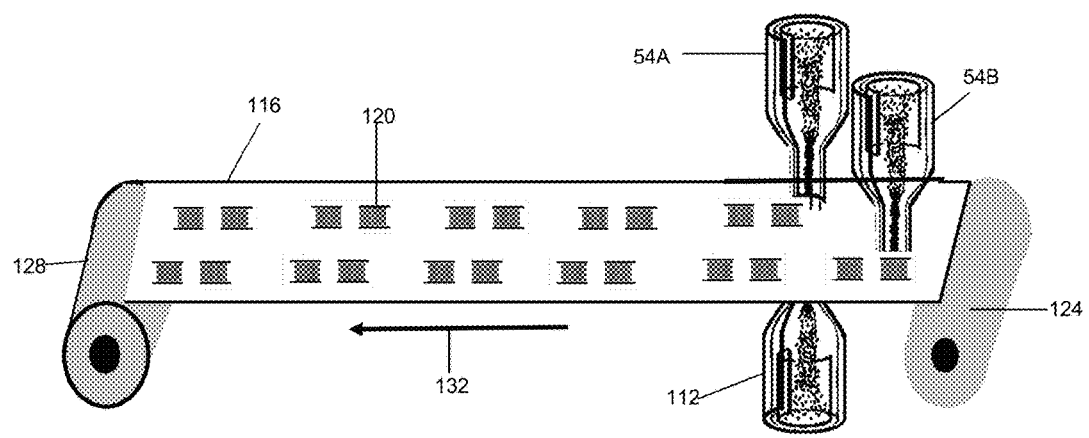
FIG. 5 is a schematic diagram of multi-head printing on both top and bottom surfaces of moving media.

FIG. 5 is a schematic diagram of multi-head printing on both top and bottom surfaces of moving media. Multiple print heads such as print heads 54A and 54B can be provided to print sensors 120 onto substrate 116. The substrate 116 can be in the form of a film which moves from roll 124 to roll 128 in a roll-to-roll printing process. A print head 112 can be provided on an underside of the substrate 116 such that sensors can be printed simultaneously on both sides of the substrate 116, or components of sensors can be printed on opposing sides of the substrate 116, such as sensor layers on one side and antenna layers on the opposing side. The substrate 116 can be moved in the direction of arrow 132 such that a succession of sensors 120 can be rapidly printed. The process can also be configured to move vertically from roll to roll.

Figure 6:
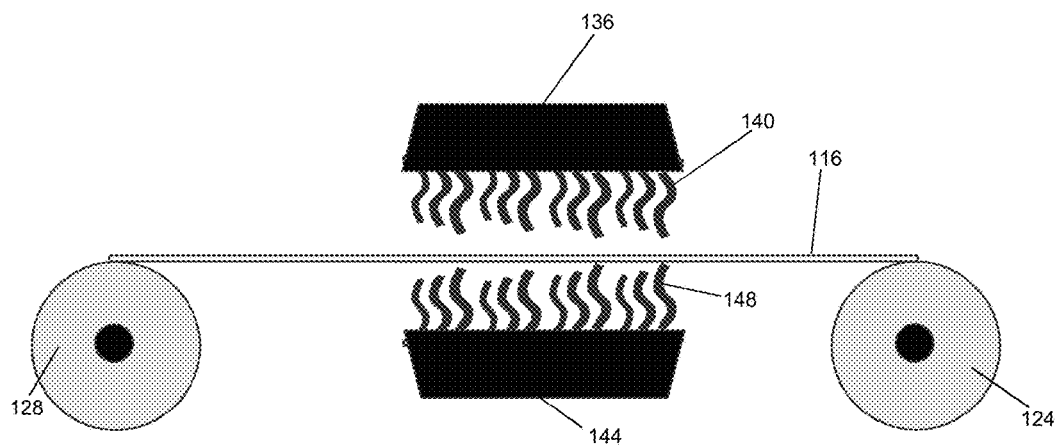
FIG. 6 is a schematic diagram illustrating pulsed thermal processing of printed surface acoustic wave structures.

FIG. 6 is a schematic diagram illustrating pulsed thermal processing devices 136 and 144 emitting high intensity radiation 140 and 148 respectively to effect curing of the sensor layers on the substrate 116.

Figures 7A, 7B:
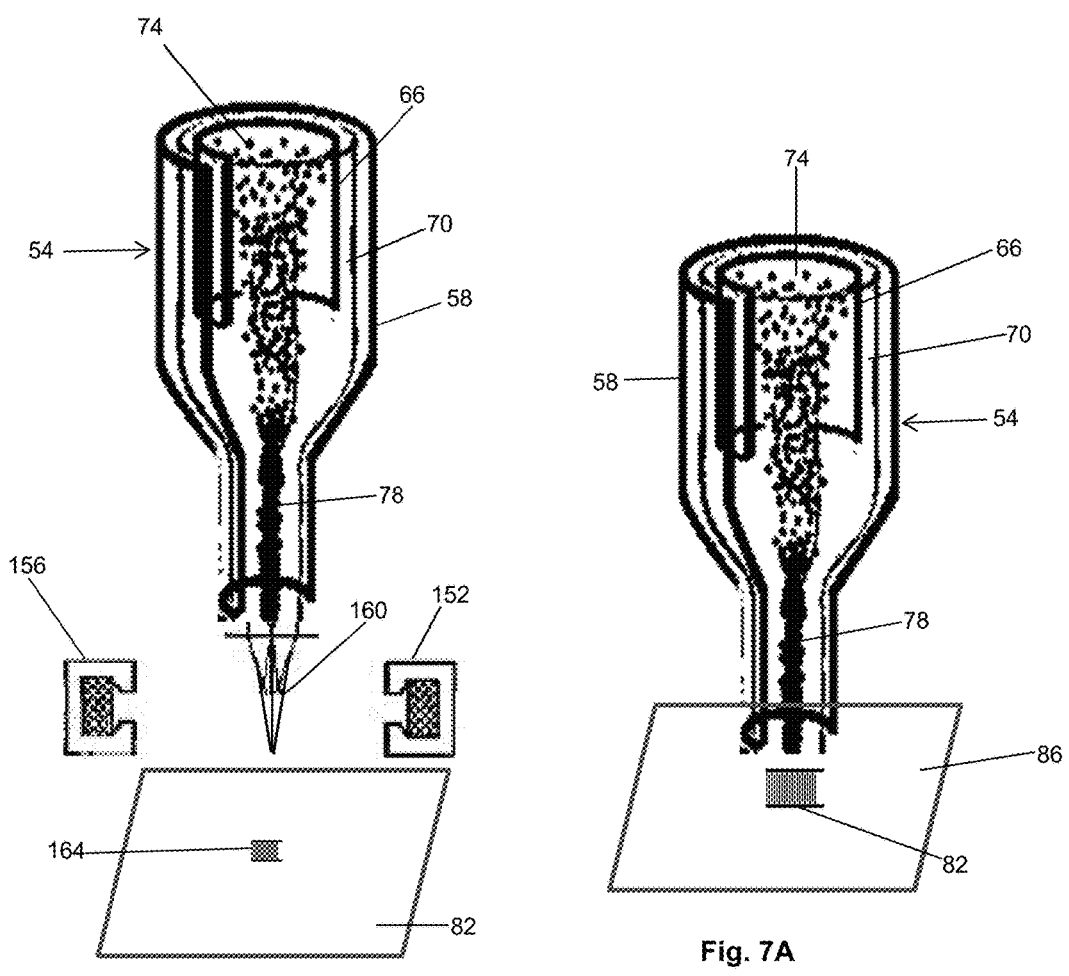
FIG. 7A is a schematic diagram of standard aerosol jet printing and FIG. 7B is a schematic diagram of aerosol jet printing augmented by electrostatic/electromagnetic focusing.

FIG. 7 is a schematic diagram of (FIG. 7A) of a standard aerosol jet print head and (FIG. 7 B) aerosol jet printing augmented by electrostatic/electromagnetic focusing. The focusing can be by any suitable structure such as electromagnets 152, 156 which focus the jet 78 to a very fine micro jet 160 enabling printing of features less than 10 µm in extent.

Figure 8:
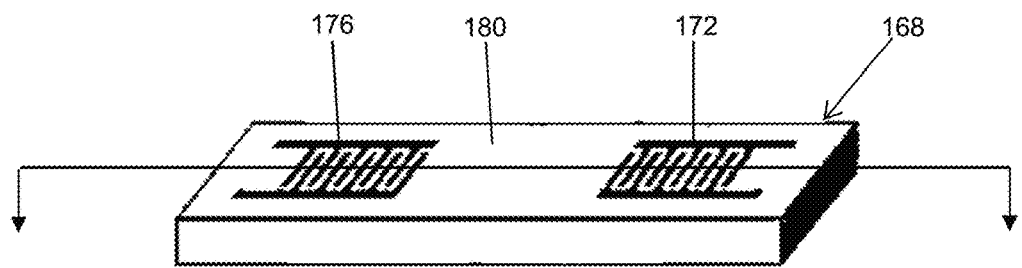
FIG. 8 is a perspective schematic view of a surface acoustic wave device.
Figure 9:
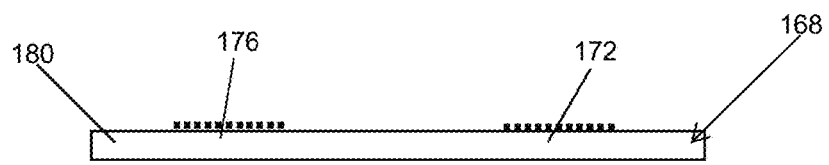
FIG. 9 is a cross-section of the surface acoustic wave device.

FIG. 8 is a perspective schematic view of a surface acoustic wave device 180 having interdigitated transducers 172 and 176 printed on piezoelectric substrate 168. FIG. 9 is a cross-section of the surface acoustic wave device 180.

Figure 10:
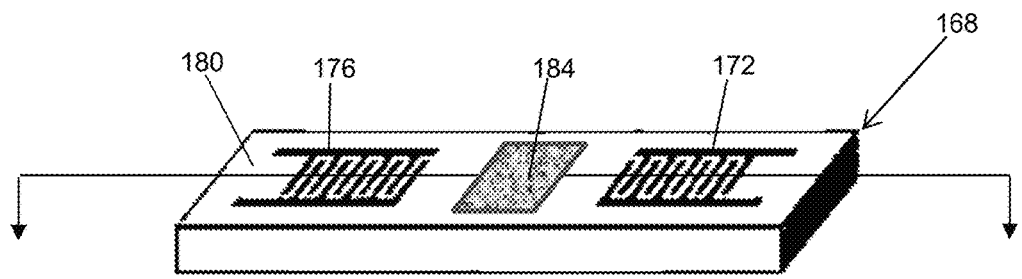
FIG. 10 is a perspective schematic view of a surface acoustic wave device with functionalizing film.
Figure 11:
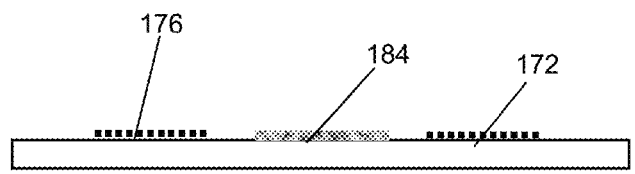
FIG. 11 is a cross-section.

FIG. 10 is a perspective schematic view of the surface acoustic wave device 168 having substrate 180 with interdigitated transducers 172 and 176, and with functionalizing film 184. The functionalizing film 184 can also be applied by aerosol jet printing. As seen in FIG. 11, the features can be printed in a single pass of the substrate 180 past the print heads.

Figure 12:
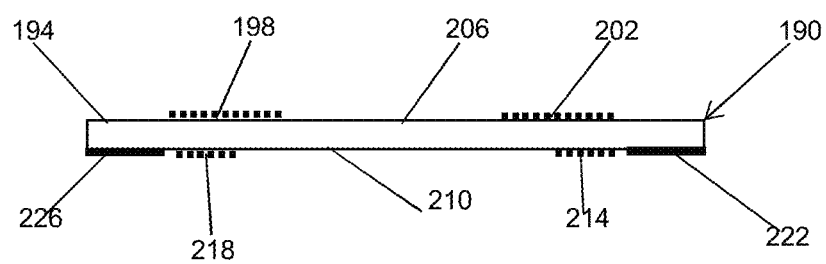
FIG. 12 is a schematic cross-section of a surface acoustic wave device with printed fractal antenna.
Figure 13:
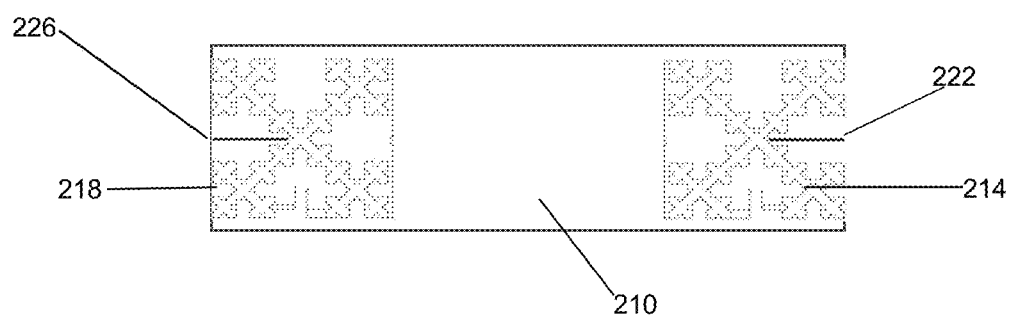
FIG. 13 is a bottom view.

FIGS. 12-13 are a schematic cross-section and bottom view of a surface acoustic wave device 190 in which a substrate 194 has interdigitated transducers 198 and 202 printed on a $1^{st}$ side 206. A $2^{nd}$ side 210 of the substrate 194 has printed thereon antennas 214 and 218. Multiple sensors can be connected to the same antenna. The antenna 214 can have contact 222 and the antenna 218 can have contact 226 which contacts can be printed with the aerosol jet printer on a bottom side 210 of the substrate 194.

Figure 14:
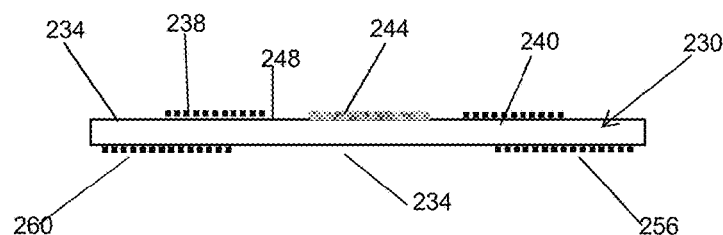
FIG. 14 is a schematic cross-section of the surface acoustic wave device with a printed spiral antenna.
Figure 15:
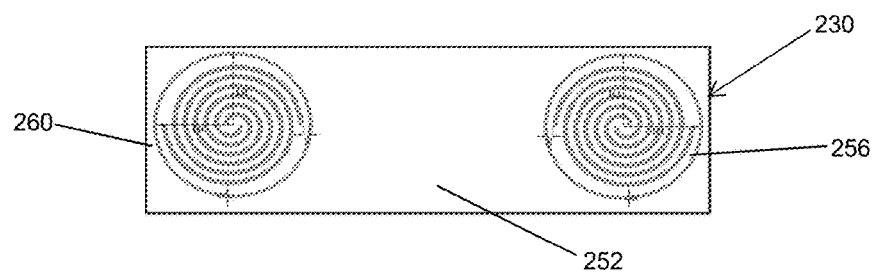
FIG. 15 is a bottom view.

FIGS. 14-15 are a schematic cross-section and bottom view of the surface acoustic wave device 230 with a having a substrate 234. Interdigitated transducers 238 and 240, and sensor film 244 can be printed on a $1^{st}$ side 248 of the substrate 234. On a $2^{nd}$ side 252 of the substrate 234 can be printed spiral antennas 256 and 260. Many different antenna designs can be printed.

Figure 16:
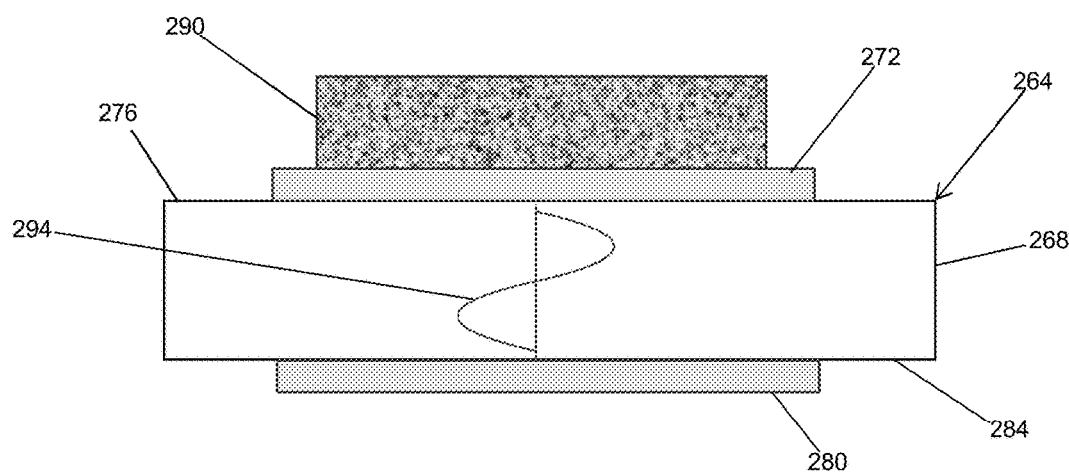
FIG. 16 is a schematic cross-section of a bulk acoustic wave device showing an acoustic wave propagating through the piezoelectric substrate, and with a functionalizing film on top of device.

FIG. 16 is a schematic cross-section of a bulk acoustic wave device 264 having a substrate 268. An interdigitated transducer 272 is provided on a $1^{st}$ side 276 of substrate 268. An interdigitated transducer 280 is provided on $2^{nd}$ side 284 of substrate 268. A functionalizing film 290 is shown on top of the $1^{st}$ interdigitated transducer 272. An acoustic wave 294 is shown propagating through the piezoelectric substrate 268. The interdigitated transducers 272 and 280, as well as functionalizing film 290 can be printed on the substrate 268 by aerosol jet printing. The Q factor of the bulk acoustic wave sensor can be greater than 1000.

Figure 17:
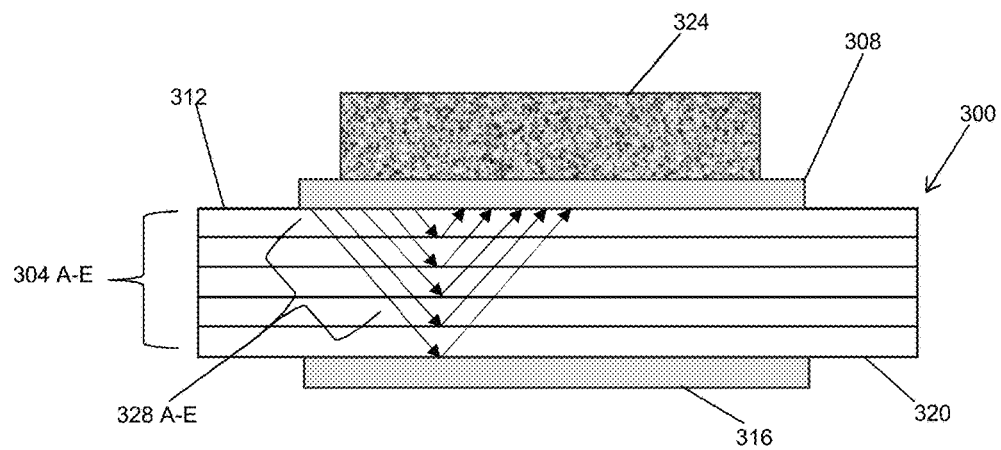
FIG. 17 is a schematic cross-section of a multi-layer bulk acoustic wave device and a string of reflected signals.

FIG. 17 is a schematic cross-section of a multi-layer bulk acoustic wave device 300 having a substrate 304 comprised of several layers 304 A-E. A $1^{st}$ interdigitated transducer 308 can be provided on a $1^{st}$ side 312 of the substrate 304. A $2^{nd}$ interdigitated transducer 316 can be provided on $2^{nd}$ side 320 of substrate 304. A functionalizing film 324 can be provided on top of the $1^{st}$ interdigitated transducer 308. The acoustic waves indicated by arrows 328 A-E can produce a string of reflected signals. All features of the device 300 can be printed on the substrate 304 by aerosol jet printing.

Figure 18:
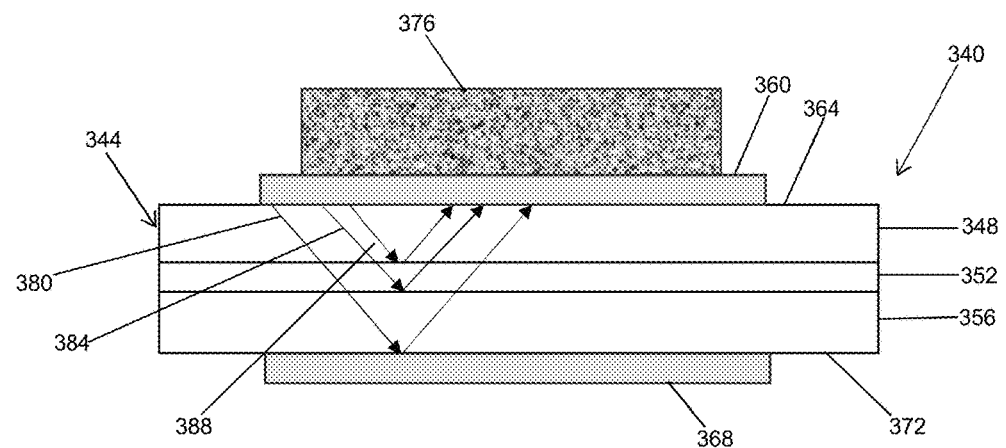
FIG. 18 is a schematic cross-section of a variable layer thickness bulk acoustic wave device providing both frequency and time diversity in reflected signals.

FIG. 18 is a schematic cross-section of a variable layer thickness bulk acoustic wave device 340 having a substrate 344. The substrate 344 is comprised of layers 348, 352, and 356 of variable layer thickness. A $1^{st}$ interdigitated transducer 360 is provided on a surface 364 of the substrate 344. A $2^{nd}$ interdigitated transducer 368 can be provided on a side 372 of the substrate 344. A functionalizing film 376 can be provided on top of the $1^{st}$ interdigitated transducer 360. Acoustic signals 380, 384, 388 will be reflected by the variable thickness layers according to the wavelengths of the signal and the properties and thickness of the layers 348, 352, and 356. The interdigitated transducers 360 and 368 and functionalizing film 376 can be printed by aerosol jet printing. The variable thickness bulk acoustic wave device 340 provides both frequency and time diversity in reflected signals.

Figure 19:
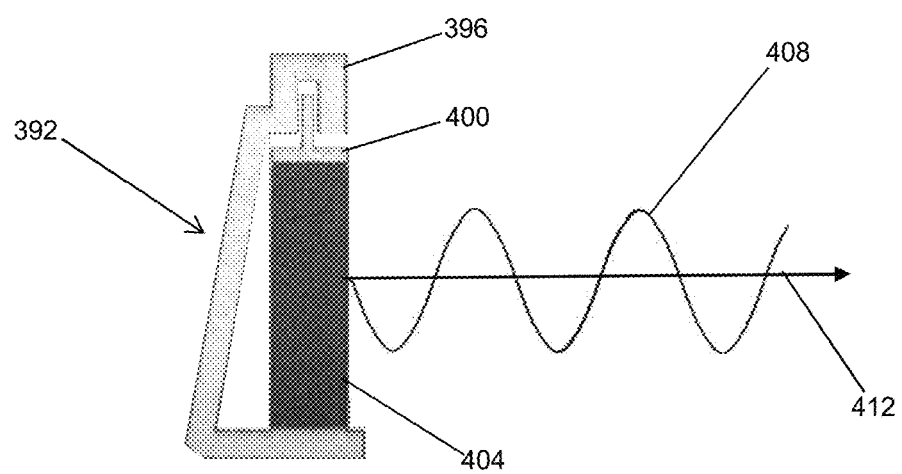
FIG. 19 is a schematic diagram of an interdigitated transducer launching an acoustic wave.
Figure 20:
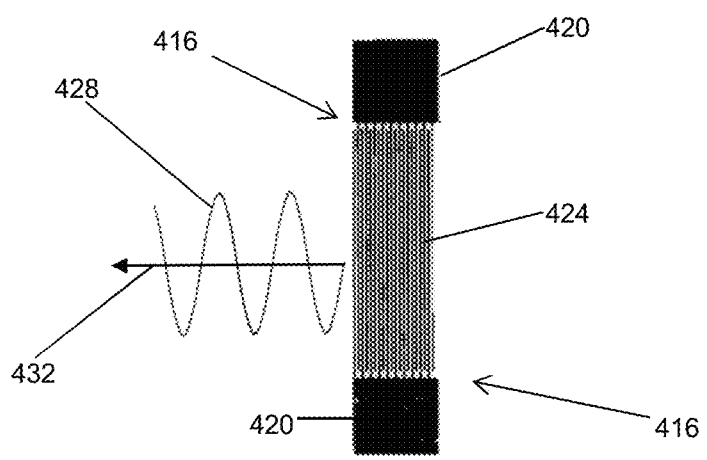
FIG. 20 is a schematic diagram of a Bragg reflector returning an acoustic signal to the interdigitated transducer.
Figure 21:
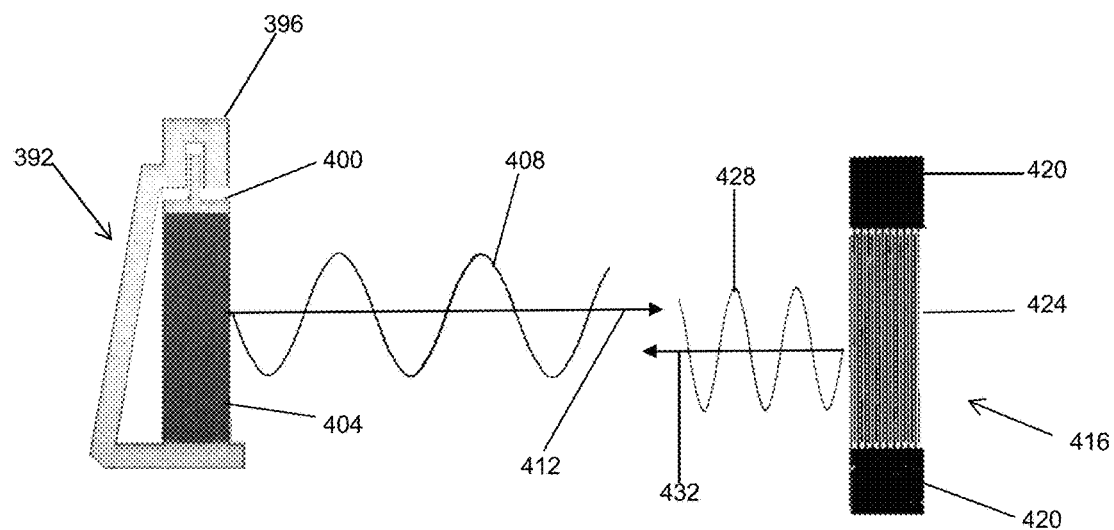
FIG. 21 is a schematic diagram of an interdigitated transducer and Bragg reflector and launched acoustic wave and reflected acoustic wave signal.
Figure 22:
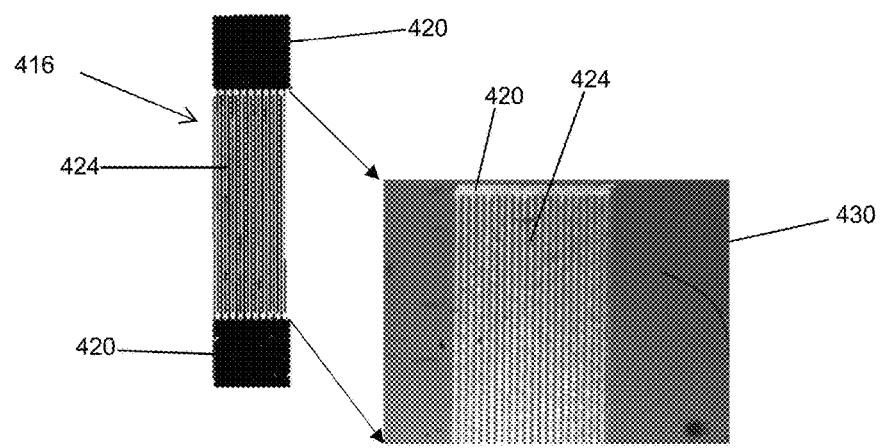
FIG. 22 is a schematic diagram and photograph of corresponding printed elements in a Bragg reflector.
Figure 23:
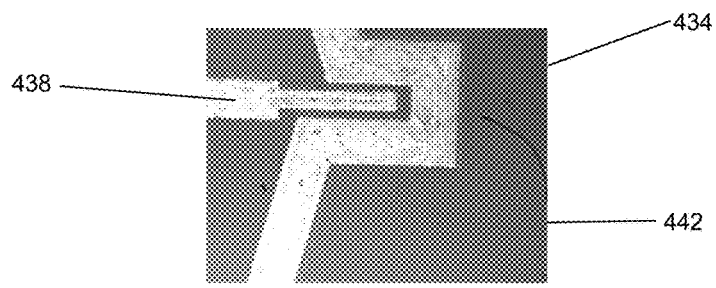
FIG. 23 is a photograph of printed interdigitated transducer electrodes.

FIG. 19 is a schematic diagram of an interdigitated transducer 392 having contacts 396 and 400 and interdigitated lines 404. An acoustic wave schematically indicated as 408 is propagated in the direction shown by arrow 412. FIG. 20 is a schematic diagram of a Bragg reflector 416 having ends 420 and reflecting layers 424. The Bragg reflector 416 selectively reflects signal 428 in the direction of arrow 432. As shown in FIG. 21, the acoustic signal 408 is emitted and returned to the interdigitated transducer 392 as reflected signal 428. As shown in FIG. 22 the Bragg reflector 416 can be printed on substrate 430 by aerosol jet printing. There is shown in FIG. 23 printed electrodes 434 and 438 of a dual channel interdigitated transducer printed on substrate 442. A series of Bragg reflectors can also be used to create an identification code. Each Bragg reflector has a unique geometry (different line width and spacing) causing a group of returned signals each having a different frequency.

Figure 24:
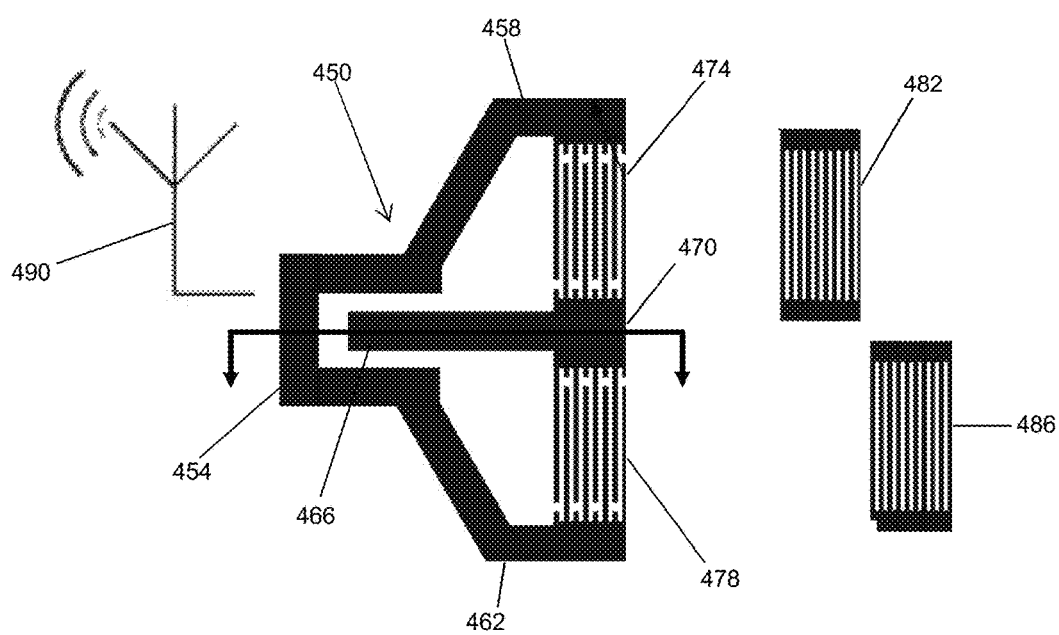
FIG. 24 is a schematic diagram of a dual channel surface acoustic wave device.
Figure 25:
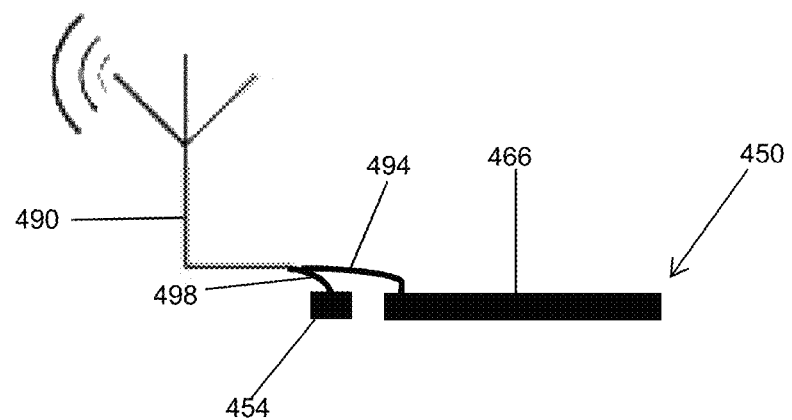
FIG. 25 is a schematic cross-section of a dual channel surface acoustic wave device showing antenna connections.

FIGS. 24-25 are a schematic diagram and cross-section of a dual channel surface acoustic wave device 450. The device 450 includes a $1^{st}$ electrode 454 having branches 458 and 462. A $2^{nd}$ electrode 466 has a terminus 470. Interdigitated transducer lines 474 and 478 are positioned between the 1st branch 458 and the terminus 470 and the 2nd branch 462 and the terminus 470. An antenna 490 can connect across the electrodes 454 and 466 to impart a signal. The antenna 490 can be connected by line 494 to electrode 466, and by line 498 to electrode 454.

Figure 26:
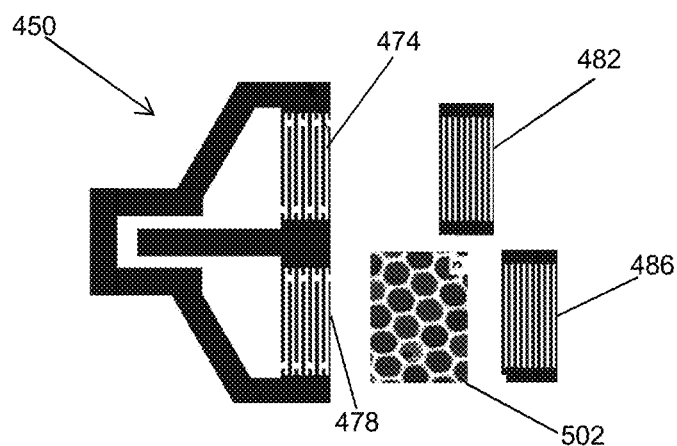
FIG. 26 is a schematic diagram of a dual channel surface acoustic wave device functionalized by hydrogel for moisture sensing.
Figure 27:
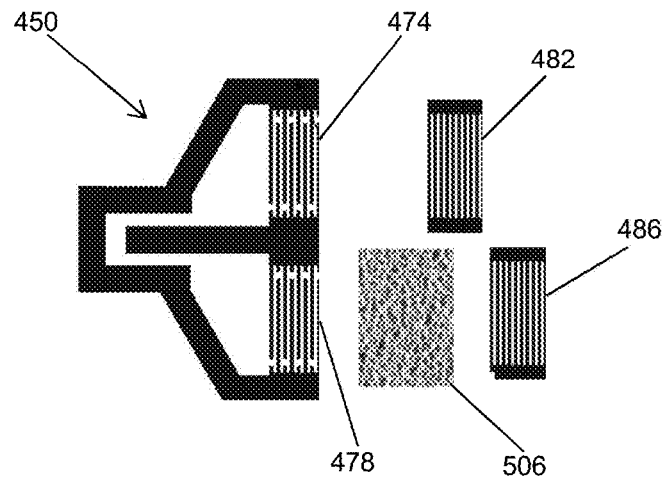
FIG. 27 is a schematic diagram of a dual channel surface acoustic wave device functionalized by a Palladium film for hydrogen sensing.
Figure 28:
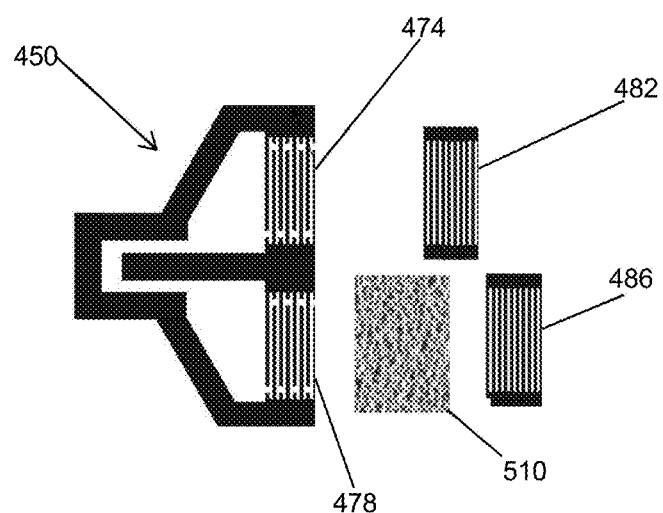
FIG. 28 is a schematic diagram of a dual channel surface acoustic wave device functionalized by graphene nanostructures for methane detection.
Figure 29:
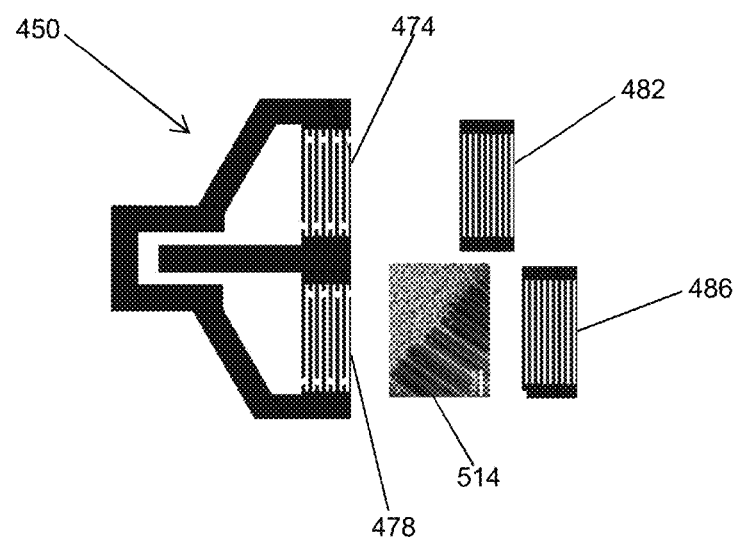
FIG. 29 is a schematic diagram of the dual channel surface acoustic wave device functionalized by carbon nanotubes for $CO_2$ detection.

FIG. 26 is a schematic diagram of the dual channel surface acoustic wave device 450 functionalized by hydrogel 502 for moisture sensing. FIG. 27 is a schematic diagram of the dual channel surface acoustic wave device 450 functionalized by a Palladium film 506 for hydrogen sensing. FIG. 28 is a schematic diagram of the dual channel surface acoustic wave device 450 functionalized by graphene nanostructures 510 for methane detection. FIG. 29 is a schematic diagram of the dual channel surface acoustic wave device functionalized by carbon nanotubes 514 for $CO_2$ detection. These films can be printed by aerosol jet printing or fabricated by other means. Functionalization can also be achieved with organic compounds called amines. Amines are derived from ammonia and can be tailored for $CO_2$ detection, for example. The amine is also printed by aerosol jet methods.

Figure 30:
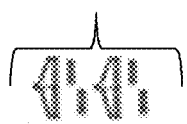
FIG. 30 is a photograph of printed dual channel surface acoustic wave devices.
Figure 31:
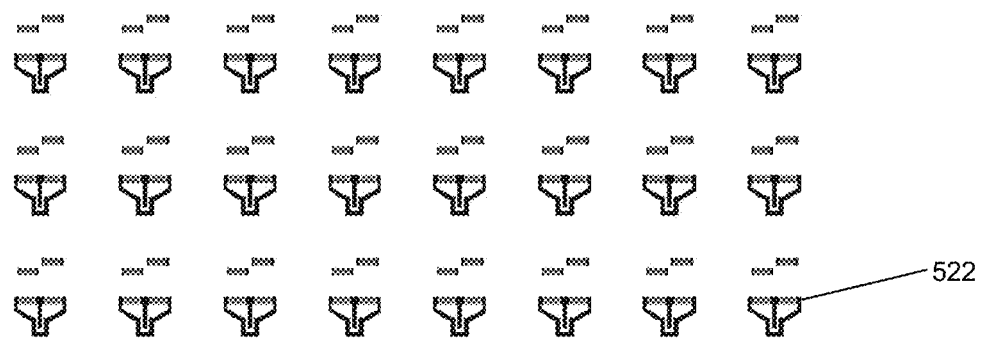
FIG. 31 is a schematic diagram illustrating an array of surface acoustic wave devices printed simultaneously and sequentially.

FIG. 30 is a photograph of printed dual channel surface acoustic wave devices 518 printed according to the invention. FIG. 31 is a schematic diagram illustrating how an array of surface acoustic wave devices 522 can be printed simultaneously and sequentially on a single substrate. Employing a printing process that implements a 2 mm² device with 2 mm pitch, results in ~2,000 devices/wafer. A 50% decrease in sensor size more than triples the number of sensors per wafer. Multiple acoustic wave sensors as in FIG. 30 can be provided for sensing different phenomena, and can be printed and combined to determine conditions or properties not able to be determined with a single acoustic wave sensor (such as to measure temperature and humidity in combination to determine dew point). An array of sensors such as shown in FIG. 31 can be used to measure the same properties, and the results combined to create a statistical result with improved accuracy over the result from a single sensor.

Figure 32:
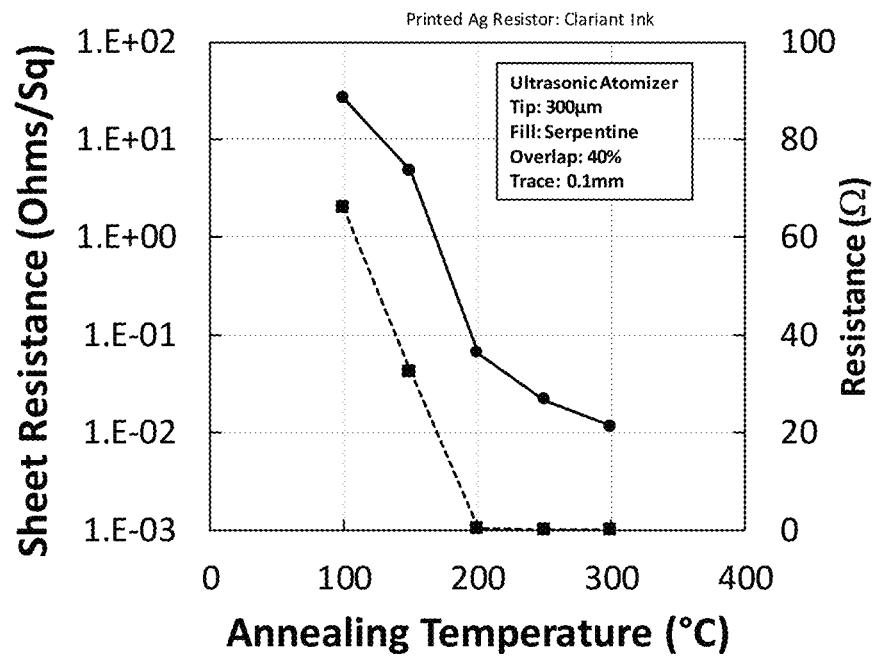
FIG. 32 is a plot of sheet resistance (ohms/Sq) versus annealing temperature (° C.) for printed structures by an ultrasonic atomizer.
Figure 33:
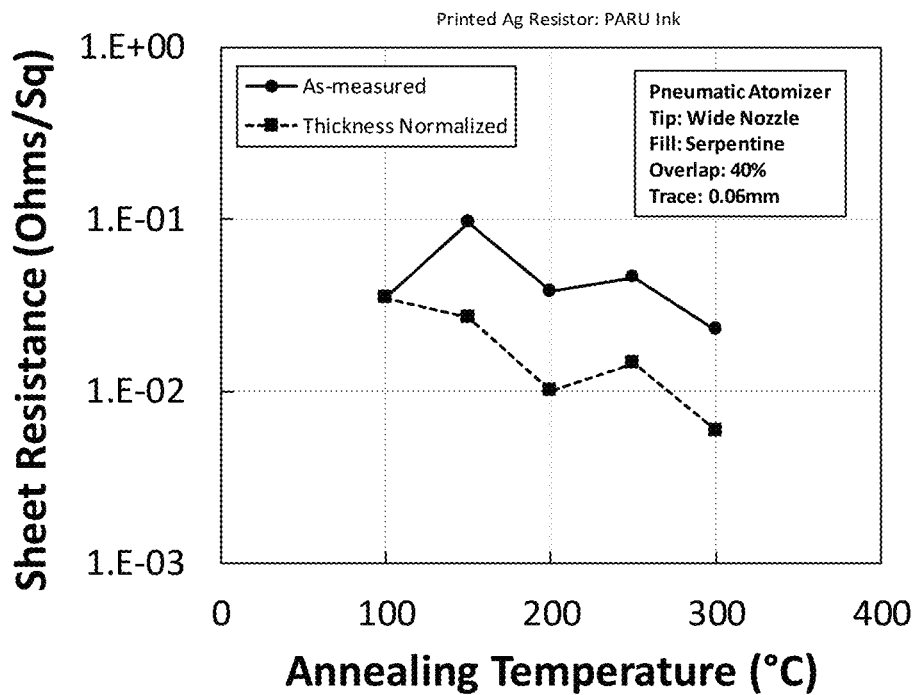
FIG. 33 is a plot of sheet resistance (ohms/Sq) versus annealing temperature (° C.) for printed structures by a pneumatic atomizer.

FIG. 32 is a plot of sheet resistance (ohms/Sq) versus annealing temperature (° C.) for structures printed by an ultrasonic atomizer. The plot shows that sheet resistance generally decreases with increasing annealing temperature. FIG. 33 is a plot of sheet resistance (ohms/Sq) versus annealing temperature (° C.) for structures printed by a pneumatic atomizer. The decrease in sheet resistance with annealing is not as pronounced for the pneumatic atomizer as for the ultrasonic atomizer.

Figure 34:
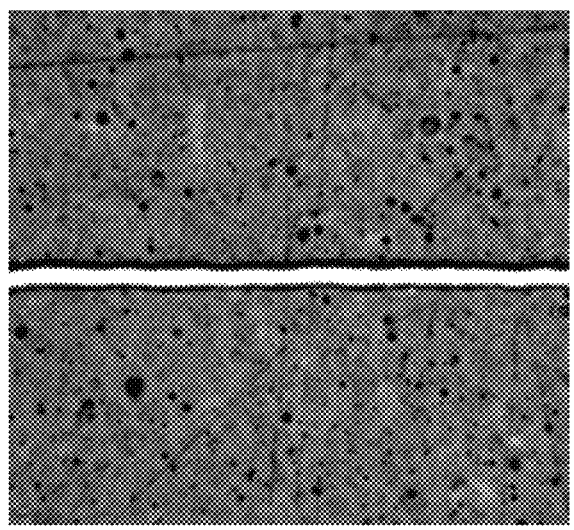
FIG. 34 is a photograph of a 10 μm line printed on a piezoelectric polymer (PV DF) substrate with 50 nm silver particles in a liquid suspension.

FIG. 34 is a photograph of a 10 μm line printed with 50 nm silver particles suspended in alcohol on a piezoelectric polymer (PVDF) substrate. This figure illustrates the very fine features that can be printed for sensors according to the invention.

Figure 35:
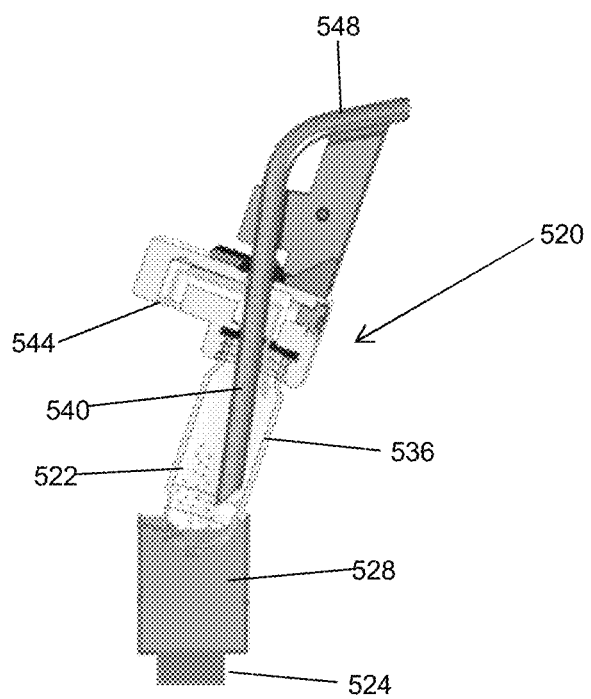
FIG. 35 is a schematic diagram of an ultrasonic atomizer print head.
Figure 36:
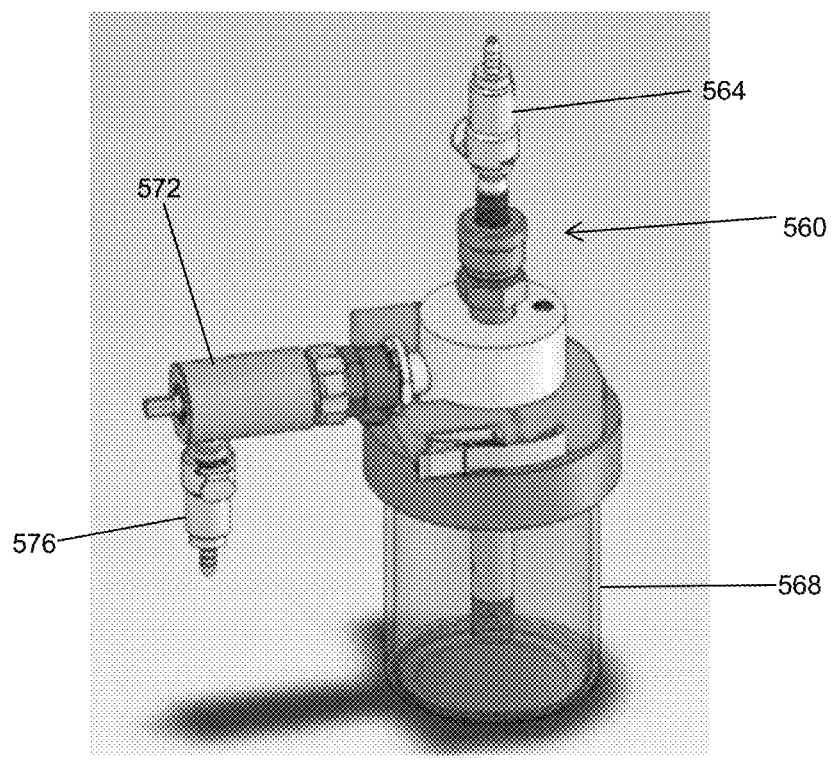
FIG. 36 is a schematic diagram of a pneumatic atomizer print head.

FIG. 35 is a schematic diagram of an ultrasonic atomizer print head assembly 520. The print head 520 includes an ultrasonic transducer 524 for applying energy to the ink bath 528. This creates droplets 522 which mix with gas from gas inlet 544 in chamber 536 and provide an aerosol in conduit 540 which exits at outlet 548 to the print head. The transducer 524 produces high-frequency pressure waves causing the ink or other liquid source material to be atomized. The atomized droplets are then entrained in the gas stream and deposited on the substrate. This device can be used for materials with viscosity in the range of 1-5 cP and particulate suspensions of 50 nm or less.

FIG. 36 is a schematic diagram of a pneumatic atomizer print head 560. Gas enters the device through gas inlet 564 and mixes with in bath 568. The aerosol so created exits at outlet 572 to the print nozzle. An exhaust 576 can also be provided. The pneumatic atomizer uses high-velocity gas stream to shear liquid ink into small droplets (1 to 5 μm). Compressed gas is expanded through the atomizer nozzle, producing a high-velocity jet. Larger droplets impact the walls, returning to the reservoir. Smaller droplets remain suspended for deposition. The pneumatic atomizer can be used for inks, pastes, or other materials with viscosity in the range of 1 to 1000 cP and particulate suspensions <500 nm in size.

The BAW/SAW sensors of the invention can be fabricated by suitable aerosol jet equipment, such as can be obtained from Optomec, Inc. (Albuquerque, N. Mex.). Other possible fabrication methods including ink jet printing, screen printing, syringe printing, plasma pray printing, and myriad fused deposition printing methods including laser and electron beam melting, are capable of printing structures that fall into a subset of aerosol jet capabilities. Aerosol jet is a highly versatile additive manufacturing tool capable of efficiently depositing metals, semi-conductors, insulators, polymers and even biological materials in precise miniature patterns or larger structures depending upon the system configuration.

SAW devices rely on precise feature size printing in order to function in recognized ISM communication frequency bands compatible with many existing process control and automation systems. The invention has achieved some of the smallest aerosol jet sensor structures to date. Both a dual channel SAW device and a Bragg reflector having ~6 um features have been produced. This feature size produces an operating frequency range of ~125-175 MHz in the resulting SAW device. Controlling the operating frequency of acoustic wave sensors is important for two reasons: a) the operating frequency largely determines the operational communication distance between the passive sensor and the interrogator; and b) tailoring the frequency response provides each sensor with a unique identity.

Fabricating BAW sensors also requires precise deposition control. BAW devices rely on precise control of device layer thickness. Aerosol jet provides ~10 nanometer layer thickness printing control. The performance of the device, commonly represented by the Q-factor, is also highly dependent on the device geometry. Aerosol jet printed BAW devices can achieve Qf>1,000, enabling detection limits as small as 1 part in $10^9$ (1 part/billion or 1 ppb). Similarly, SAW devices have also demonstrated sub-ppm detection limits.

The invention is capable of producing sensors with many different modes of sensing including: physical sensors, chemical sensors, biological sensors, location and tracking sensors, and tamper resistant seals. Possible sensor modalities include, without limitation physical sensors for temperature, strain, pressure, corrosion. Chemical sensors are used to measure humidity/moisture, $CO_2$, $CH_4$, HF, VOCs, $H_2$, and the like. Electronic sensors measure current flow, voltage and charge. Biological sensors test for food spoilage, bacterial and fungal agents, blood sugar level, and other biometric factors. Location and tracking sensors and tamper resistant seals are also becoming more common. Sensing applications include physical sensing for energy control, condition monitoring, and presence detection. Electronic sensing is performed for grid monitoring and surveillance. Chemical sensing is used for pipeline monitoring, leak/plume detection, and accident response. Multiple sensor modalities can easily be combined to produce a unique signature or finger print. Other applications are possible.

BAW and SAW sensor functionality is realized by measuring the change in the acoustic wave propagation velocity within the device substrate. The following relationship describes this phenomenon by relating the interrogator operating frequency to the acoustic propagation velocity divided by the acoustic wavelength. The physical feature size of the device (BAW—layer thickness and SAW—spatial feature size and pitch) largely determines the operating parameters.

$$v = c/\lambda \qquad (1)$$

In equation (1), v represents the electromagnetic interrogation frequency as described above. The invention is capable of printing SAW devices with 6-20 um feature size and operational frequencies ranging from 37.5-175 MHz. The device propagation velocity represented by c in equation (1) is the acoustic propagation velocity within the device substrate, not the speed of light. The acoustic velocity can range from 1,500 to nearly 4,500 m/s, depending upon substrate material selection. The $\lambda$ represents the acoustic wavelength of the device determined by layer thickness or surface features for BAW and SAW devices respectively. For SAW devices being printed currently, the Bragg reflectors and IDT include ~10 um line width and pitch. This critical feature size is generally interpreted as $\lambda/4$, the quarter-wave coupling wavelength from antenna theory.

$$v = c/(\lambda/4) = 4{,}000 \text{ m/s}/(10 \text{ um}/4) = \sim 75 \text{ MHz} \qquad (2)$$

In order to create an acoustic sensor, it is necessary to couple to the sensor substrate and modify the acoustic propagation velocity. There are two principle ways in which acoustic velocity is altered: a) mass loading—the substrate gains additional inertia through increased mass loading causing a mechanical impedance to the acoustic wave; and b) strain induced modification of the substrate elastic modulus—the acoustoelectric effect. Both phenomena result in a change of amplitude, phase, frequency or a time delay—the returned signal arrives later in time proportional to the changed mass or strain.

Surface acoustic wave devices require their substrate to be a ferroelectric material. More specifically, piezoelectric substrate materials such as lead-zirconate-titanate (PZT), lithium niobate, or quartz produce the greatest response or conversion efficiency. Polymeric substrates, such as polyvinyladene fluoride (PVDF), also exhibits ferroelectric properties, allowing acoustic devices to be printed upon flexible substrates. Other materials are possible.

Piezoelectric materials exhibit temperature dependent response, hence a SAW device functions as a temperature sensor without further functionalization. To sense other physical variables, the SAW device is functionalized by mechanical means. For instance, a very sensitive pressure sensor is created by functionalizing the SAW device by making the substrate a flexible element or diaphragm. This flexing is caused by changing pressure, creating a changing strain in the substrate that is detected as an acoustic velocity shift in the SAW device.

Sensing chemical or biological variables requires functionalization in a different manner. Humidity sensing is a relatively simple example of functionalization via mass loading. Polymethylmethacrilate (PMMA), is a reversible hydrophilic material that is readily printed by AJ methods. Hydrophilic aerogels can also be printed. FIG. 26 illustrates a SAW humidity sensor architecture. The hydrophilic region is deposited into one of the SAW device channels. An acoustic velocity change occurs as moisture loading changes. As the film increases in mass, the acoustic velocity decreases, and vise versa.

Many film treatments are possible to functionalize the SAW device. Phase separated glass and metal oxide structures provide a scaffold having extremely high surface area. These high surface area structures are then functionalized by creating chemically specific absorption sites, such as, palladium nanoparticles for hydrogen sensing. A nanostructured spinodally phase separated ultra-porous silica film can be deposited on lithium niobate.

The sensor design and functionalization methods can be utilized with a single aerosol jet deposition head or multiple heads. The sensor designs can be scaled-up for roll-to-roll processing by employing a multi-head approach. Aerosol jet deposition can be performed with a parallel head array, but additional head arrays can also be performing additional fabrication steps down stream. A variety of materials can be printed, including conductors, insulators, semi-conductors, dielectrics, and biological materials. Feature sizes less than ~10 μm and with no real upper limit are possible. The method is compatible with rigid and flexible substrates. The integration of sensors, antennas, and electronics is possible, with a wide range of operating communications frequencies Key controls include ink selection (viscosity, conductor, insulator and dielectric), substrate selection (material, thickness, wafer or polymer film, deposition rate, nozzle size, atomization carrier gas pressure and flow rate, sheath gas pressure and flow rate, exhaust gas pressure and flow rate, scanning speed and thermal management.

EXAMPLE

Surface acoustic wave (SAW) sensors were developed using aerosol jet direct digital printing, employing an Optomec AJ200 system. Single channel and dual channel sensors were demonstrated. Sensor modalities include temperature, humidity and $CO_2$. Volatile organic compound (VOC) sensors and other physical sensors such as pressure, corrosion, current and voltage are possible. The invention allows printing features as small as 5 microns, and feature size to 1 micron or less are possible. In order to fabricate these sensors, several parameters must be controlled. A 100 micron nozzle, combined with 25 ccm aerosol flow rate from an ultrasonic atomizer (UA) was utilized. The UA was set to 0.3 mA, with a nitrogen sheath gas flow rate of 22 ccm. The processing speed was 1 mm/sec, depositing Clariant silver colloid 25 ink with on a lithium niobate substrate. The total print time was 2 minutes.

The ease and low cost of manufacture of sensors created by the invention present the possibility of disposable sensors. Disposable sensors create a paradigm shift in measurement, control, monitoring, etc. by opening up new methods and approaches. For example, sensors embedded into products during manufacturing, sensors that are embedded into the manufacturing devices/equipment for intimate process monitoring, and sensors that flow-through the manufacturing process on test articles or the actual product itself, can be used to characterize process conditions in situ. Gaining intimate knowledge of manufacturing process conditions has never been done in this way and could lead to significant efficiency gains. Further, having process knowledge, item-by-item has also never been achieved and could be exploited for efficiency gains. For example, many thousand sheets of drywall are manufactured on a daily basis. The condition of the sheet versus the process could be measured providing pinpoint information of actual product condition, versus global process information. Disposable RF/SAW sensors could be applied to each sheet of drywall, monitoring in real-time, the temperature and moisture content of the sheet. Process conditions, such as oven temperature, residence time, etc. are then controlled in response to optimum product conditions instead of being controlled to a global fixed point.

There are many advantages of aerosol jet printing versus inkjet and screen printing. There is a wider possible material range (metals, alloys, resistor paste, dielectrics, polymers, adhesives). Most materials are standard off-the-shelf. There is no customization that is required. Significantly higher metal loadings are possible, as much as 50%-70 weight percent for high resolution printing. There is a 10 times smaller nano-particle droplet size to produce finer features. There is 20-30 times higher yield than inkjet per nozzle. There are higher volumetric rates and metal loading. There is superior throughput nozzle with higher material loading per droplet. There is 5 times the distance above substrate enables conformal printing on non-planar surfaces. There are much finer feature sizes (10 μm) and tighter pitch (20 μm) pitch. There is better edge definition.

There are many advantages of aerosol jet printing versus screen printing. Noncontact printing eliminates breakage of substrates. Noncontact process enables conformal printing on non-planar substrates. The aerosol jet process is easier to implement changes, and there is no hard tooling. Thinner layer deposits reduced material waste. Much finer feature size (10 μm) and tighter pitch (20 μm) are possible.

Direct printing of conductive patterns eliminates the use of toxic chemicals and saves costs. Nano silver conductive inks allow direct printing of conductive patterns for electronic devices on any surface. Hazardous chemical metallization processes are replaced by water-based ink containing metal particles to form the electronic pattern. Nano-sized silver particles can be cured at low temperatures to create an electric conductor almost as conductive as a pure silver wire.

I claim:

1. An acoustic wave sensor, comprising:
   a piezoelectric substrate layer;
   a sensor layer joined to the substrate layer and comprising a first interdigitated acoustic wave transducer and at least one other feature selected from the group consisting of a sensing film, an interdigitated acoustic wave transducer, and a Bragg reflector;
   wherein all of the interdigitated acoustic wave transducers and Bragg reflector are aerosol jet printed;
   an antenna layer and an insulation layer interposed between the antenna layer and the sensor layer, wherein the insulation layer and antenna layer are aerosol jet printed; and,
   wherein at least one of the sensor layer and antenna layer comprise a dielectric matrix material.

2. An acoustic wave sensor, comprising:
   a piezoelectric substrate layer;
   a sensor layer joined to the substrate layer and comprising a first interdigitated acoustic wave transducer and at least one other feature selected from the group consisting of a sensing film, an interdigitated acoustic wave transducer, and a Bragg reflector;
   wherein all of the interdigitated acoustic wave transducers and Bragg reflector are aerosol jet printed;
   an antenna layer and an insulation layer interposed between the antenna layer and the sensor layer, wherein the insulation layer and antenna layer are aerosol jet printed; and,
   wherein the sensor layer and the antenna layer are printed on opposing sides of the piezoelectric substrate layer.

* * * * *